United States Patent [19]

Hermanson

[11] 4,089,552
[45] May 16, 1978

[54] CONTACT LENS LOCATION FINDER

[76] Inventor: William A. Hermanson, 3700 Galt Ocean Dr., Ft. Lauderdale, Fla. 33308

[21] Appl. No.: 786,577

[22] Filed: Apr. 11, 1977

[51] Int. Cl.² ............................................. A61F 9/00
[52] U.S. Cl. ................................. 294/1 CA; 206/5.1
[58] Field of Search ........... 294/1 R, 1 CA, 25, 27 R, 294/32; 51/216 LP, 216 H; 128/303 R; 206/.8, .81, 5.1; 248/1, 346, DIG. 2; 269/321 R, 321 CF; 350/245–247; 351/38, 40, 155

[56] References Cited

U.S. PATENT DOCUMENTS

| | | | |
|---|---|---|---|
| 3,031,918 | 5/1962 | Moyers | 294/27 R |
| 3,037,616 | 6/1962 | Phipps | 206/5.1 |
| 3,584,908 | 6/1971 | Ray | 294/1 CA |
| 3,768,633 | 10/1973 | Nathan | 206/5.1 |

*Primary Examiner*—Johnny D. Cherry
*Attorney, Agent, or Firm*—Oltman and Flynn

[57] ABSTRACT

To assist a person with seriously impaired vision to manually locate and pick up a contact lens, a flat, smooth surfaced pad of aerated polyethylene is provided, having a narrow bridge segment on which the convex surface of the lens rests and enlargements at opposite ends of the bridge segment. The width of the bridge segment is equal to the outside diameter of the lens. The pad contains titanium dioxide, which gives it a stark white color that makes the pad more visible and makes it easier to see the contact lens on the pad. The pad can be doubled over for convenient storage in a small envelope or the like, and when removed it springs back immediately into its normal flat shape.

6 Claims, 6 Drawing Figures

CONTACT LENS LOCATION FINDER

BACKGROUND OF THE INVENTION

The purpose of this invention is to facilitate the insertion of a hard contact lens in his or her eye by a person termed, in the language of ophthalmologists, Monocular Aphakes. Such a person has been operated on one eye for removal of a natural lens having a condition known as a cataract. More specifically the invention applies to a Monocular Aphake who also has a cataract condition in his other eye in which the protein matter has become macromolecular and inflexible to a stage described as "legal blindness." This bilateral condition prevents reading, on a standard eye chart, letters which are directly below the largest letters on the top line of the chart from a distance of 20 feet. This is known as 20/200 vision.

Hard contact lenses are molded from methyl methacrylate, a transparent resin. This lens is shaped like a tiny bowl to fit the curvature of the pupil and iris of the eye. The outside diameter of the bowl is 10 mm. Being transparent, the lens cannot be seen by persons having the specific vision problems described. Such a person can locate the lens only by the sense of touch in the fingers. Consequently, the lens very frequently is lost while such a person is feeling for it on any surface under any degree of illumination.

It is customary practice before inserting the lens in the post-cataract eye to place one or preferably two drops of a contact lens wetting solution into the tiny bowl of the lens to provide a lubricant and adherent film to the surface of the eye. The post-cataract eye cannot focus. Thus it becomes impossible for a Monocular Aphake, except by mere chance, to deposit the drops precisely in the bowl. This is unfortunate because the reflection of light from the surface of the drops in this bowl constitutes the only means by which the lens can be located. The lack of focus and the mist which obscure both the legally blinded vision and the post-cataract eye make it guess work to see the bowl or its periphery. Its outline must be clearly seen in order to grasp it between the forefinger or middle finger and thumb so that it may be transferred to the cushion of the forefinger or the middle finger of the opposite hand before insertion into the eye with the drops kept in the bowl.

Another problem for the contact lens wearer is asepsis. Eye infections frequently result from contact lenses being laid on bacteria prone surfaces. Whether travelling, engaged in work, sports or business, the wearer of the lenses is subject to experiences which require that they be removed from the eye. Dustmotes, hairs, wind, chemicals, cosmetics, etc. make a lens unbearable until removed and a drop or two of wetting solution added after removal of the irritant. A clean surface is hard to find away from home, for example, in an automobile, train, restaurant, office or factory.

SUMMARY OF THE INVENTION

To overcome the foregoing problems I have devised a novel device for assisting a Monocular Aphake or other contact lens wearer with seriously impaired vision to locate the contact lens by manual touch and lift it with one hand and transfer it to the other hand without spilling the drops before using that other hand to insert the lens in his or her eye.

The present device is a thin, flat pad of aerated polyethylene with very smooth opposite major faces that are heat sealed for water repellency. The pad has a narrow bridge segment extending between larger opposite end segments. The width of this bridge segment preferably is equal to the outside diameter of the contact lens, and it has a length betwwen the larger end segments which preferably is at least three times its width. The opposite longitudinal edges of the bridge segment serve as guides or feelers for the thumb and either the forefinger or middle finger of one hand, enabling the user to locate the lens on the bridge entirely by manual touch and to pick up the lens without spilling the drops that have been inserted in it.

The pad preferably contains a brightening material, preferably titanium dioxide, to enhance its visibility and the visibility of the contact lens placed on it.

The pad is readily flexible so that it can easily be folded transversely at its bridge segment for storage doubled over in a small envelope or other container with its enlarged end segments in confronting relationship to one another. When removed from this container the pad springs back to its normal shape due to its inherent resilience.

A principal object of this invention is to provide a novel and improved device for assisting a person with seriously impaired vision to locate manually and pick up a contact lens.

Another object of this invention is to provide such a device which assists the user to insert drops in the contact lens and then to pick up the lens without losing the drops from the lens.

Further objects and advantages of this invention will be apparent from the following detailed description of a presently-preferred embodiment thereof, which is shown in the accompanying drawings in which.

Figure 1:
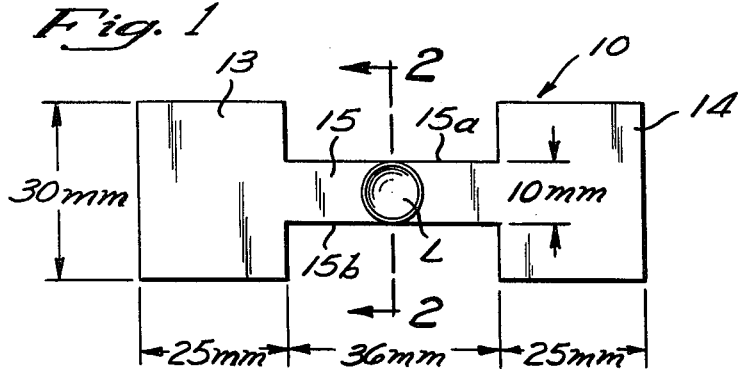
FIG. 1 is a top plan view of the device supporting a contact lens.
Figure 2:
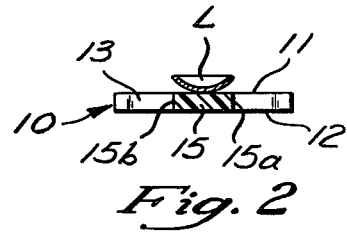
FIG. 2 is a section taken along the line 2—2 in FIG. 1.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

Referring to the drawing, the presently-preferred embodiment of this invention is a thin, flat pad 10 of polyethylene which has been aerated or expanded by a suitable aerosol. The opposite major faces 11 and 12 of the pad are heat sealed for water repellency and they are very smooth and non-abrasive. The entire pad is easily flexible manually and is resilient so that after being folded it can immediately spring back to its normal flat shape when free to do so.

The pad has a uniform thickness of substantially ⅛ inch throughout its extent. In the embodiment illustrated the length of the pad is 86 mm. At its opposite ends the pad has rectangular enlargements 13 and 14, each of which is 25 mm. long and 30 mm. wide. Between these end enlargements the pad presents a narrow bridge segment 15 which is 36 mm. long and 10 mm. wide. This bridge segment is integrally connected centrally to each end enlargement, so that each end enlargement projects transversely beyond the bridge segment 10 mm. in either direction.

The pad is pigmented with titanium dioxide which gives it a stark white color to make it visible even under low illumination.

Figure 3:
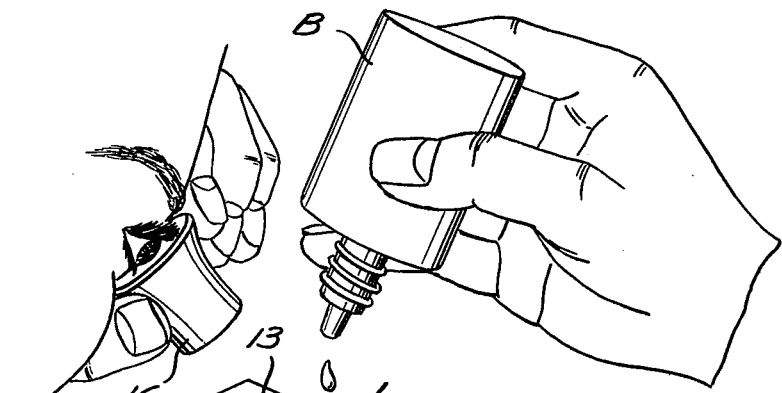
FIG. 3 is a perspective view showing the user putting drops in the lens on the present device.
Figure 5:
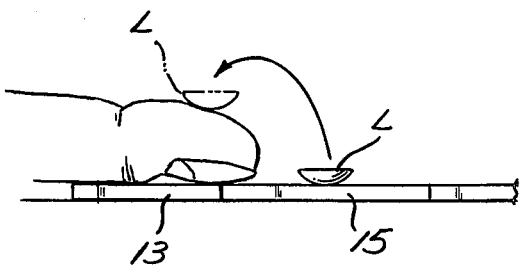
FIG. 5 is an elevation showing schematically the transfer of the lens from the present device to a finger of the other hand.

As shown in FIG. 3 the contact lens L is placed on the pad with the convex surface of the lens resting on top of the narrow bridge segment 15 of the pad. The user may insert drops into the lens from an inverted bottle B held in one hand and using a jeweler's eye loupe 16, held in the other hand, as a magnifying viewer. Typically, such an eye loupe has a magnification of 5 times or 7 times and has a 21 mm. wide field. For most users this provides sufficient focus to make visible the outline of the contact lens resting on the narrow bridge segment 15 of the pad.

The width of this bridge segment is equal to the outside diameter (10 mm.) of the contact lens, so that the opposite longitudinal edges 15a and 15b of this bridge segment serve as guide surfaces or feelers for the user's thumb and either the forefinger or middle finger of one hand, enabling the user to locate the lens with assurance even though he cannot see it well. The narrowness of the bridge segment 15 and its uniform width prevent tipping of the lens.

Figure 4:
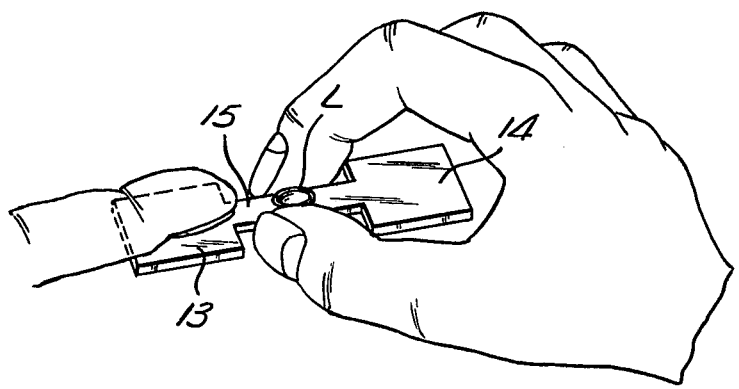
FIG. 4 is a perspective view showing the user removing the lens from the present device.

Grasping the lens between the thumb and either the forefinger or middle finger of one hand, the user now may lift the lens from the pad without spilling the drops from the lens. The forefinger or middle finger of the second hand may be positioned as shown in FIG. 4, with the posterior phalanges of that finger resting flat on the adjacent end enlargement 13 or 14 of the pad, and with the anterior cushion of this finger facing upward and located over or close to the bridge segment 15 so that the lens may be placed on it, again without spilling the drops. This hand may now be used to insert the contact lens in the eye.

It should be understood that when the finger of the second hand rests on the end enlargement of the pad this has the effect of stabilizing the pad against sliding or slipping on the support surface on which it is resting. To position this finger in this fashion comes very naturally, virtually reflexively, as I have learned by personal experience, and the end enlargement of the pad serves as a guide for this finger which helps the user to position it properly with respect to the first hand which is lifting the lens up from the pad.

Thus, the particular shape of the present pad aids each of the user's hands to position themselves properly, solely by touch and without the aid of the eyes, for the required operations.

In the embodiment shown the length of the bridge segment 15 is 3.6 times its width. I prefer that its length be not less than 3 times the width in order to provide room for the thumb and forefinger or middle finger to be properly guided by the respective opposite longitudinal edges of the bridge segment, regardless of where the lens may happen to be positioned along the length of the bridge segment.

Figure 6:
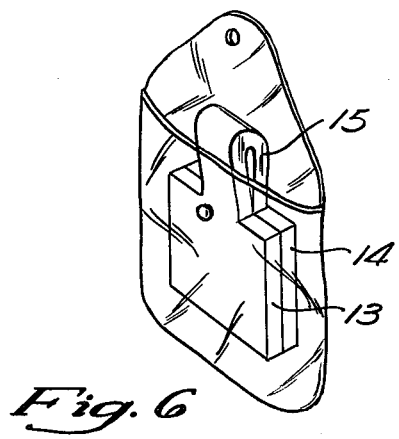
FIG. 6 shows the present device folded up in an envelope.

As shown in FIG. 6, when not in use the pad may be doubled over and inserted into a small, relatively flat envelope or the like, with the opposite end enlargements 13 and 14 of the pad in close, confronting relationship to one another in the envelope and the bridge segment 15 folded transversely midway along its length. The pad is flexible enough to be folded in half readily but when it is taken out of the envelope its natural resilience causes the pad to spring back immediately to its normal flat shape.

The material of the pad is critically important, and aerated polyethylene is the only material I have found completely suitable for this purpose. Among other materials I have tried, polyurethane does not have the desired surface slickness, polystyrene in the thickness desired here tends to crack when folded, and vinyls are too firm to have the resilience desired.

The heat sealed major faces of the present pad are easy to keep clean because of their slickness and water repellency. Consequently, the problem of asepsis is minimized because this pad provides a clean support on which the contact lens may be placed when removed from the eye at any time required.

The present pad can be manufactured at a relatively low cost, and it saves the user the cost of replacing a contact lens lost because of the user's difficulty in locating it prior to inserting it in the eye.

I claim:

1. A device for assisting a person with impaired vision to manually locate and grasp a bowl-shaped hard contact lens for the person's eye, said device being a flat, one-piece pad of aerated polyethylene having a narrow bridge segment and enlarged segments at the opposite ends of the bridge segment, said pad having smooth opposite major faces which are heat sealed and water repellent, said pad being of substantially uniform thickness between its opposite major faces, said bridge segment having a width substantially equal to the outside diameter of the lens and having a length between said enlarged end segments which is substantially greater than the outside diameter of the lens, whereby the lens with its convex surface resting on said bridge segment is readily locatable by the person's thumb and forefinger or middle finger of one hand guided by the opposite longitudinal edges of the bridge segment while the person's other hand engages one of said enlarged ends, said pad being easily flexible manually at said bridge segment to be folded transversely midway along the bridge segment for storage in a container with said enlarged end segments in face-to-face confronting relationship to one another, said pad being sufficiently resilient to spring back to its flat shape when removed from the container.

2. A device according to claim 1, wherein said pad contains a brightening material.

3. A device according to claim 2, wherein said brightening material is titanium dioxide which imparts a stark white color to the pad to make it visible under low illumination.

4. A device according to claim 3, wherein said bridge segment has a uniform width of substantially 10 mm. and has a length between said enlarged end segments of at least three times its width.

5. A device according to claim 4, wherein each of said enlarged end segments projects transversely beyond both opposite longitudinal edges of the bridge segment.

6. A device according to claim 1, wherein said bridge segment has a substantially uniform width of 10 mm. and has a length between said enlarged end segments of at least three times its width.

* * * * *